(12) United States Patent
Dai et al.

(10) Patent No.: US 8,975,331 B2
(45) Date of Patent: Mar. 10, 2015

(54) BIODEGRADABLE AND BIOCOMPATIBLE WATERBORNE POLYURETHANE

(75) Inventors: Shenghong A. Dai, Taichung (TW);
Chien-Wen Chen, Taichung (TW);
You-Sing Chen, Taichung (TW);
Shan-Hui Hsu, Taipei (TW)

(73) Assignees: Great Eastern Resins Industrial Co., Ltd., Taichung (TW); National Chung Hsing University, Taichung (TW)

( * ) Notice: Subject to any disclaimer, the term of this patent is extended or adjusted under 35 U.S.C. 154(b) by 588 days.

(21) Appl. No.: 13/317,651

(22) Filed: Oct. 25, 2011

(65) Prior Publication Data

US 2012/0108742 A1    May 3, 2012

(30) Foreign Application Priority Data

Oct. 28, 2010   (TW) ................................ 99137054 A

(51) Int. Cl.
| | | |
|---|---|---|
| C08G 18/08 | (2006.01) | |
| C08L 33/00 | (2006.01) | |
| C08G 18/42 | (2006.01) | |
| A61L 15/26 | (2006.01) | |
| A61L 15/64 | (2006.01) | |
| C08G 18/12 | (2006.01) | |
| C08G 18/75 | (2006.01) | |

(52) U.S. Cl.
CPC ............... *C08G 18/428* (2013.01); *A61L 15/26* (2013.01); *A61L 15/64* (2013.01); *C08G 18/0823* (2013.01); *C08G 18/0866* (2013.01); *C08G 18/12* (2013.01); *C08G 18/4202* (2013.01); *C08G 18/4238* (2013.01); *C08G 18/755* (2013.01); *C08G 2230/00* (2013.01)
USPC .......................................... 524/591; 523/523

(58) Field of Classification Search
USPC .................................................. 524/591, 523
See application file for complete search history.

(56) References Cited

U.S. PATENT DOCUMENTS

| | | | |
|---|---|---|---|
| 6,123,963 A | 9/2000 | Kim et al. | |
| 6,372,876 B1 * | 4/2002 | Kim et al. ...................... | 528/71 |
| 2009/0192283 A1 | 7/2009 | Dai et al. | |
| 2010/0055471 A1 * | 3/2010 | Fuhry ........................... | 428/419 |

FOREIGN PATENT DOCUMENTS

CN           1220288 A      6/1999

OTHER PUBLICATIONS

Office Action from Taiwanese Patent Office of TW 200932771A which corresponds to US Publication No. 2009/0192283 Application No. 06 770 683.8 dated Apr. 29, 2013.
Wenshou Wang et al., "Polylactide-based polyurethane and its shape-memory behavior", European Polymer Journal, No. 42 (2006), pp. 1240-1249.
Wenshou Wang et al., "Shape memory effect of poly(L-lactide)-based polyurethanes with different hard segments", Polym Int, 56:840-846 (2007).

* cited by examiner

*Primary Examiner* — Aiqun Li
(74) *Attorney, Agent, or Firm* — Juan Carlos A. Marquez; Bacon & Thomas PLLC

(57) ABSTRACT

The present invention relates to a waterborne polyurethane containing biodegradable segments and the process for synthesizing the same. The waterborne polyurethane according to the present invention has excellent biodegradable, biocompatible and mechanical characteristics and thus is a useful biomedical material, in particular for making films for medical applications.

9 Claims, 1 Drawing Sheet

BIODEGRADABLE AND BIOCOMPATIBLE WATERBORNE POLYURETHANE

FIELD OF THE INVENTION

The present invention relates to a waterborne polyurethane which has excellent biodegradability, biocompatibility and mechanical properties.

BACKGROUND OF THE INVENTION

Polyurethane (PU) has been widely used in commodities due to its abrasion resistance, flexibility and mechanical strength.

Conventionally, PU is prepared by a solvent method. In the solvent method, a significant amount of organic solvents is required, and this not only increases the level of hazardous volatile organic compounds (VOCs) in the product but also raises dependency on fossil fuel. Due to these drawbacks, the solvent method is gradually being replaced by a newly-developed method in which waterborne polyurethane is synthesized. Detailed descriptions of synthesis of waterborne polyurethane can be found in, for example, US Patent Publication No. 2009-0192283.

PU products are not degradable when disposed in the natural environment, and thus treatments such as incineration or landfill are necessary. This increases handling cost and could become a serious environmental problem. To reduce the potential damage to the environment, researchers have attempted to incorporate biodegradable polymeric intermediates into PU. Among the biodegradable polymeric intermediates, polylactide diol is one of the most promising materials. A common scheme is to react lactide with short-chain diols or dicarboxylic acids to replace the terminal functional group of the lactide with hydroxy or carboxylic group by ring-opening polymerization. The molecular weight of the polylactide diols or dicarboxylic acids is controlled by the molar ratio of the initiators to the monomers.

However, it is reported that satisfactory mechanical properties, for example elongation higher than 25%, are not obtainable by merely reacting a single polylactide diol and isocyanate; see Wenshou Wang et al., "Shape memory effect of poly(L-lactide)-based polyurethanes with different hard segments," Polymer International, Vol. 56, pp. 840-846 (2007)).

To resolve the above problem as well as to satisfy the needs for a healthy, environmentally friendly and economical material, the present invention discloses an environmentally friendly method in which biodegradable chains and other long-chain polyols are incorporated into polyurethane to provide a polymer with satisfactory mechanical properties, biodegradability and biocompatibility.

SUMMARY OF THE INVENTION

One aspect of the present invention provides a process for synthesizing a waterborne polyurethane containing biodegradable segments. The process comprises the steps of:
(1) mixing two or more long-chain polyols at 80 to 120° C., wherein at least one polyol is a biodegradable long-chain polyol;
(2) adding to the mixture obtained in (1) one or more aliphatic diisocyanates and reacting to form a pre-polymer A;
(3) adding a hydrophilic component and a water-soluble solvent with a boiling point of 50 to 80° C. and reacting at a temperature between 45° C. and the boiling point of the water-soluble solvent to form a pre-polymer B;
(4) optionally adding to the pre-polymer B a neutralizer;
(5) dispersing the mixture obtained in (4) in water to form a water-dispersed mixture; and
(6) adding polyamines so as to increase the molecular weight of the pre-polymer dispersed in water; wherein in steps (1) to (3), the ratio of the total NCO functional groups to the total OH functional groups is in a range of 1.3 to 2.6.

Another aspect of the present invention provides a waterborne polyurethane comprising biodegradable segments prepared by the aforesaid process.

Further aspect of the present invention provides a waterborne polyurethane containing biodegradable segments. The waterborne polyurethane essentially consists of:
15 to 45 wt % biodegradable long-chain polyols, based on the total solid contents, while the total amount of long-chain polyols is 60 to 75 wt % based on the total solid contents; and
25 to 40 wt % other components, based on the total solid contents, including aliphatic diisocyanates, hydrophilic components and polyamines.

DETAILED DESCRIPTION OF THE INVENTION

Figure 1:
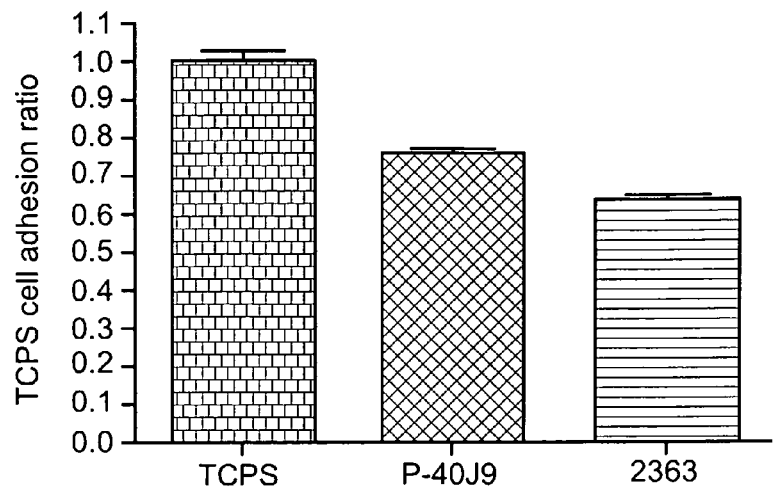
FIG. 1 shows the results of the cell adhesion test for cross-linked waterborne polyurethane film in Experiment 10.

In the process according to the present invention, it is preferred that the ratio of the amino equivalent of the polyamines to the equivalent of the isocyanate functional group in the pre-polymer B is 70 to 100 mole %.

In the method according to the present invention, long-chain polyols, which serve as soft blocks, should be straight-chain predominant. Suitable long-chain polyols include but are not limited to esters, ethers, carbonates, olefins and the mixtures thereof. The long-chain polyols preferably have a number-average molecular weight of 1,000 to 4,000 g/mol. The average number of functional groups is about 1.5 to 2.5, preferably 2.

Preferably, the long-chain polyols in the present invention include two types: (1) commercial long-chain polyols commonly used for manufacturing polyurethane, which are normally derived from products of petroleum cracking and are not biodegradable or have a very low biodegradability; and (2) biodegradable long-chain polyols, which are derived from natural materials, e.g., corn. In the present invention, at least one long-chain polyol is biodegradable so that the biodegradability of the waterborne polyurethane to be synthesized is provided. All conventional biodegradable long-chain polyols may be used in the present invention, and long-chain polyols comprising polylactic acid (PLA) units and/or polyglycolic acid units are preferred.

Biodegradable long-chain polyols can be synthesized by the following process: providing a short-chain diol having a molecular weight of 60 to 600 g/mol as an initiator; reacting the short-chain diol with L-lactide, D,L-lactide, D-lactide, glycolide or a mixture thereof by ring-opening polymerization to obtain a long-chain diol. Details on such process can be seen in, for example, Wenshou Wang et al, "Polylactide-based polyurethane and its shape-memory behavior," European Polymer Journal Vol. 42, pp. 1240-1249 (2006). In the examples shown below, poly-(L-lactide) diol (PLLA diol) is used.

In the process of the present invention, the amount of biodegradable long-chain polyols should be 15 to 45 wt %, based on the total solid contents. The amount of total long-chain polyols should be 60 to 75 wt %, based on the total solid contents. Insufficient biodegradable long-chain polyols result in low biodegradability of the synthesized polymer while biodegradable long-chain polyols in an excess amount result in poor film-forming property of the synthesized polymer.

In the process of the present invention, the aliphatic diisocyanates can be 4,4'-methylenebis(cyclohexyl isocyanate) ($H_{12}MDI$), isophorone diisocyanate (IPDI), 1,6-hexane diisocyanate (HDI), 1,6-hexane diisocyanate dimer (HDI dimer), xylylene diisocyanate (XDI) or a mixture thereof.

The hydrophilic components used in the present invention can be compounds having hydrophilic functional groups, or chain segments, or a mixture thereof and include (but are not limited to) carboxylic acids or carboxylates, sulphonic acids or sulfonates, phosphoric acids or phosphates, chain segments of polyvinyl ether, and mixtures thereof. To be specific, the hydrophilic components include but are not limited to dimethylol propionic acid (DMPA), dimethylol butyric acid (DMBA), N-(2-hydroxyethyl)taurine monosodium salt, sodium 1,4-butanediol-2-sulfonate, polyvinyl ether sulfonate diamine, polyvinyl ether sulfonate diol, and mixtures thereof. The hydrophilic components are preferably in an amount of 2.5 to 5.0 wt %, based on the total solid contents.

The water-soluble solvents used in the present invention preferably have a boiling point of 50 to 80° C. Ketones are preferred, particularly butanone. These solvents have boiling points lower than that of water, so recovery by distillation and reuse become applicable.

If the hydrophilic functional groups in the hydrophilic components used in the present invention are not neutralized (for example, acids are selected as hydrophilic components), neutralizer should be added thereto for transforming the hydrophilic components into salts so as to make the prepolymer water-dispersible. Suitable neutralizer can be selected from triethylamine (TEA), ammonium hydroxide, sodium hydroxide, potassium hydroxide or a mixture thereof. To ensure that the pre-polymer has sufficient water dispersibility, the equivalents of the hydrophilic components and the neutralizers should be within a range of 0.9 to 1.1.

The polyamines used in the present invention include chain extenders and optional cross-linkers.

Preferred chain extenders are diamine chain extenders and can be selected from ethylene diamine (EDA), butylene diamine, hexylene diamine, isophorone diamine, p-phenylene diamine, m-xylylene-α,α'-diamine, p-xylylene-α,α'-diamine, oligo(alkylene)ether diamine with a molecular weight of 100-250, 1,4-cyclohexanedimethanamine, 1,3-cyclohexanedimethanamine, meta-phenylenediamine (mPDA), trans/cis-(1,4-cyclohexanediamine), [R,S]/[R,R]-(1,3-cyclohexanediamine), trans-(4-aminomethyl-1-cyclohexanamine), 3-(aminomethyl)cyclohexylamine, 2,5-norbornanebis(methylamine), 2,6-norbornanebis(methylamine), and mixtures thereof. The oligo(alkylene)ether diamine contains repeat units and alkyl amine end groups, the repeat units may be (but are not limited to) ethenoxyethene, propanoxypropane or a mixture thereof, and the alkyl amine end groups may be (but are not limited to) ethylene amine, propylene amine or a mixture thereof.

Preferred cross-linkers used in the present invention are amines having three functional groups, such as Jeffamine® T-403 (Huntsman, US). The amine equivalents in the cross-linkers are 3-20% of the total amine equivalents.

In addition, one aspect of the present invention provides a waterborne polyurethane comprising biodegradable segments prepared by the aforesaid process.

The biodegradable segments-containing waterborne polyurethane prepared by the process of the present invention also has the following properties:

The waterborne polyurethane emulsion has a pH value of 7.0 to 10.0; the diameter of the particles in the waterborne polyurethane emulsion is 20 to 200 nm.

Another aspect of the present invention provides a waterborne polyurethane containing biodegradable segments. The waterborne polyurethane essentially consists of:

15 to 45 wt % biodegradable long-chain polyols, based on the total solid contents, while the total amount of long-chain polyols is 60 to 75 wt % based on the total solid contents; and 25 to 40 wt % other components, based on the total solid contents, including aliphatic diisocyanates, hydrophilic components and polyamines.

In one embodiment of the present invention, the biodegradable segments-containing waterborne polyurethane has an elongation of 200% to 600%.

Another aspect of the present invention provides a biodegradable and biocompatible film comprising the waterborne polyurethane according to the present invention. The film is particularly suitable for making health care products including wound dressings, tissue anti-adhesion films, surface coatings for plastic or paper materials and disposable health care products such as packaging bags and isolated films. In addition, the biodegradable segments-containing waterborne polyurethane can be also used as material for medical products such as tubes or pipes.

The details of the present invention are further described with reference to the following examples. Such description is not intended to limit the scope of the present invention. Any modifications and changes made by those skilled in the art without departing from the spirit of the present invention will fall within the scope of the present invention.

EXAMPLES

Experiment 1 Synthesis of Poly-(L-Lactide) Diol

The poly-(L-lactide) diol (PLLA diol) used in the present invention can be synthesized according to a suitable conventional process. For example, one may apply the following process:

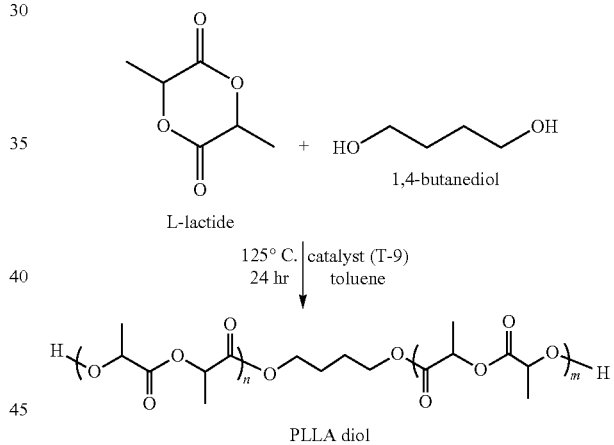

SCHEME 1

Adding catalyst T-9 (Tin(II) 2-ethylhexanoate) (0.66 g' 1.658×10$^{-3}$ mol) and initiators 1,4-butanediol (48.23 g' 0.535 mol) to toluene (40 ml) in a flask to obtain a dispersion. Adding the dispersion to a 3-L three-necked flask containing L-lactide (1000 g' 6.94 mol). Washing the flask by toluene and adding the residual toluene (total 1000 ml) in a reactor. Stirring the mixture by a magnetic agitator under nitrogen. A Dean-Stark trap was connected to the condenser tube to remove residual moisture, and the temperature of the oil bath was controlled at 125° C. to reflux the toluene for 24 hrs. After the reaction was completed, the mixture was cooled to 60 to 70° C. Rapidly dripping ethanol (about 10,000 ml) into the mixture and mechanically agitating (500 rpm) for precipitation and conducting solid/liquid separation by centrifugal apparatus (6,000 rpm, 3 min). Collecting and drying solids in a vacuum oven at 40° C. for 48 hrs. After the sample was completely dried, grinding it to obtain poly-(L-lactide) diol in white powder form with 63 wt % purity. Sealing the product and keeping it at 0° C. The results of the molecular weight and thermal analysis of the obtained poly-(L-lactide) diol are as shown in the following TABLES 1 and 2:

TABLE 1

|  | $Mn_{(theo.)}$ (g/mol) | $Mn^a_{(NMR)}$ (g/mol) | $Mn^b_{(Titr.)}$ (g/mol) | $Mn^c_{(GPC)}$ (g/mol) | $Mw^c_{(GPC)}$ (g/mol) | $PD^c$ | Yield (%) |
|---|---|---|---|---|---|---|---|
| PLLA diol | 1,985 | 2,096 | 2,356 | 5,255 | 6,225 | 1.18 | 63 |

[a] Analyzed by 1H-NMR.
[b] Determined by titration of the mole number of PLLA diol end functional groups.
[c] Analyzed by GPC(Mobile phase: DMAc, Standard: Polystyrene)

TABLE 2

|  | $T_d$ (° C.)[a] | $T_g$ (° C.)[b] | $T_c$ (° C.)[b] | $T_m$ (° C.)[b] |
|---|---|---|---|---|
| PLLA diol | 209 | 25 | 90 | 109 |

[a] Decomposition temperature at 5 wt % loss (Td) was measured by TGA with a constant heating rate of 10° C./min under $N_2$.
[b] DSC was operated with a constant heating rate of 10° C./min under $N_2$. Temperatures were determined by the exothermic/endothermic change during the second time the sample was being heated.

Experiment 2 Synthesis of Waterborne Polyurethane (P-0)

RS-956 (polyester diol from adipic acid, butanediol, ethanediol, OH: 56.1, MW: about 2,000 g/mol; Yong Shun Chem. Co. Ltd, Taiwan) (70 g, 0.035 mol) and catalyst T-9 (0.1 g, 2.47×10$^{-1}$ mol) were added to a 500 ml lid-separable four-necked reactor and heated up to 110° C. The reactant was mechanically agitated at a rotary speed of 180 rpm until the reactant became transparent liquid. IPDI (29.56 g, 0.133 mol) was added to the reactant which was then reacted at 110° C. for 3 hrs. The mixture was cooled down to 75° C. DMPA (4.69 g, 0.035 mol) was dispersed to butanone (26.06 g) and the mixture was added to a reactor. The mixture was reacted for 1 hr at 75° C. and then cooled to 50° C. TEA (3.54 g, 0.035 mol) was added for neutralization for 30 mins. The mixture was cooled at 45° C. and rotary speed elevated to 1030 rpm. Double distilled water was rapidly added to the mixture. After the water was dispersed, water-diluted chain extender EDA (3.22 g, 0.054 mol) was added and reacted for 30 mins to obtain a waterborne polyurethane emulsion with solid contents of about 30 wt %.

Experiment 3 Synthesis of Waterborne Polyurethane (P-20)

The procedures and reaction conditions described in Experiment 2 were applied, except that 20 wt % (14 g, 0.007 mol) polyester diol (RS-956) was replaced with 20 wt % poly-(L-lactide) diol (as prepared in Experiment 1).

Experiment 4 Synthesis of Waterborne Polyurethane (P-40)

The procedures and reaction conditions described in Experiment 2 were applied, except that 40 wt % (28 g, 0.013 mol) polyester diol (RS-956) was replaced with 40 wt % poly-(L-lactide) diol (as prepared in Experiment 1).

Experiment 5 Synthesis of Waterborne Polyurethane (P-60)

The procedures and reaction conditions described in Experiment 2 were applied, except that 60 wt % (42 g, 0.020 mol) polyester diol (RS-956) was replaced with 60 wt % poly-(L-lactide) diol (as prepared in Experiment 1).

Experiment 6 Synthesis of Waterborne Polyurethane (P-80)

The procedures and reaction conditions described in Experiment 2 were applied, except that 80 wt % (56 g, 0.027 mol) polyester diol (RS-956) was replaced with 80 wt % poly-(L-lactide) diol (as prepared in Experiment 1).

Experiment 7 Synthesis of Waterborne Polyurethane (P-100)

The procedures and reaction conditions described in Experiment 2 were applied, but the polyester diol (RS-956) was completely replaced with 70 g (0.033 mol) poly-(L-lactide) diol as prepared in Experiment 1.

The basic properties, thermal properties, molecular weight and mechanical properties of the waterborne polyurethane solution are as shown in Tables 3 and 4.

TABLE 3

|  | Sample | | | | | |
|---|---|---|---|---|---|---|
|  | P-0 | P-20 | P-40 | P-60 | P-80 | P-100 |
| pH[a] | 8.2 | 7.8 | 7.5 | 7.8 | 8.3 | 9.2 |
| viscosity (cPs.)[b] | 15 | 14 | 14 | 27 | 14 | 25 |
| particle size (nm)[c] | 56 | 31 | 51 | 59 | 53 | 72 |

[a] Determined by pH meter at room temperature (about 25-27° C.).
[b] Determined by viscosity analyzer at room temperature (about 25-27° C.).
[c] Determined by particle size analyzer at a fixed temperature of 25° C.

TABLE 4

|  | P-0 | P-20 | P-40 | P-60 | P-80 | P-100 |
|---|---|---|---|---|---|---|
| $T_{d(5\%)}$ (° C.)[a] | 259 | 246 | 234 | 235 | 228 | 210 |
| DSC $T_g$ (° C.)[b] | −49 | −44 | −30 | −17 | 2 | 27 |
| DMA (tan D) $T_g$ (° C.)[c] | −31 | −6 | 10 | 41 | N/A[f] | N/A[f] |
| Mn (g/mol)[d] | N/A[f] | N/A[f] | N/A[f] | 54,165 | 20,284 | 4,616 |
| Mw (g/mol)[d] | N/A[f] | N/A[f] | N/A[f] | 466,412 | 81,422 | 62,418 |
| PDI[d] | N/A[f] | N/A | N/A[f] | 8.6 | 4.0 | 13.5 |
| Elongation (%)[e] | 385 | 379 | 274 | 217 | N/A[f] | N/A[f] |
| Tensile strength(MPa)[e] | 28.4 | 36.8 | 34.4 | 24.3 | N/A[f] | N/A[f] |
| 100% Module (MPa)[e] | 4.7 | 6.9 | 14.7 | 16.9 | N/A[f] | N/A[f] |

[a] Decomposition temperature at 5 wt % loss was determined with a constant heating rate of 10° C./min under $N_2$.
[b] Determined by the exothermic/endothermic change with a constant heating rate of 10° C./min under $N_2$ during the second time the same was being heated.
[c] Sample was tested with a constant heating rate of 2° C./min under $N_2$ in tension mode. Frequency: 1 Hz.
[d] Mobile Phase: NMP, Standard: Polystyrene.
[e] Sample was cut into dumpbell shape (ASTM D-421 type-D) and tested with a stretch rate of 100 mm/min.
[f] Unable to form a film at room temperature.

Experiment 8 Hydrolysis Test of Waterborne Polyurethane Film

Three samples for each of the polymeric products synthesized in Experiments 2 to 7 were subjected to a hydrolysis test. The films were cut into small pieces of 0.5 g and then immersed in (1) 3 wt %. NaOH and (2) phosphate buffered solution (PBS) of pH 7.4. The samples were put in an oven with a constant temperature of 37° C. After 4, 8, 12 and 24 hrs, the samples immersed in NaOH solution were washed several times by double distilled water, and then put in a vacuum oven at 40° C. for 8 hrs. Weight was measured and residual weight percentage was calculated using the following formula:

$$\text{residual weight percentage (\%):} = 100 - \left(\frac{W_o - W_t}{W_o}\right) \times 100, \quad \text{equation (1)}$$

wherein
$W_o$=initial weight of sample (g),
Wt=weight of dried sample after immersion for a specific period.

The samples immersed in PBS were tested after 10, 20 and 30 days and subjected to the same washing and drying procedures. Residual weight percentages were calculated.

The test results in 3 wt % NaOH and PBS are shown in Tables 5 and 6, respectively.

TABLE 5

| time (hr) | P-0 | P-20 | P-40 | P-60 | P-80 | P-100 |
|---|---|---|---|---|---|---|
| 0 (wt %) | 100 | 100 | 100 | 100 | 100 | 100 |
| 4 (wt %) | 93 | 85 | 71 | 64 | 22 | 12 |
| 8 (wt %) | 92 | 87 | 64 | 59 | 11 | 0 |
| 12 (wt %) | 92 | 83 | 63 | 52 | 10 | 0 |
| 24 (wt %) | 96 | 74 | 46 | 43 | 6 | 0 |

TABLE 6

| day | P-0 | P-20 | P-40 | P-60 | P-80 | P-100 |
|---|---|---|---|---|---|---|
| 0 (wt %) | 100 | 100 | 100 | 100 | 100 | 100 |
| 10 (wt %) | N/A[a] | N/A[a] | 90.0 | 87.3 | 85.7 | 84.3 |
| 20 (wt %) | N/A[a] | N/A[a] | 89.9 | 86.8 | 85.0 | 84.2 |
| 30 (wt %) | N/A[a] | N/A[a] | 88.9 | 86.5 | 84.6 | 83.7 |

[a]After 10 days of immersion in PBS, the waterborne polyurethane film was decomposed and became emulsion dispersed in the buffer solution Experiment 9 Synthesis of Cross-Linked Waterborne Polyurethane PLLA diol (28 g, 0.013 mol), RS-956 (42 g, 0.0021 mol) and catalyst T-9 (0.1 g, $2.47 \times 10^{-4}$ mol) were added to a 500 ml lid-separable four-necked reactor and heated to 110° C. The reactants were mechanically agitated at a rotary speed of 180 rpm until the reactants became transparent liquid. IPDI (29.28 g, 0.132 mol) was added to the reactants and reacted at 110° C. for 3 hrs, followed by cooling to 75° C. DMPA (4.69 g, 0.035 mol) was dispersed to butanone (26.06 g) and the mixture was added to the reactor. The mixture was reacted at 75° C. for 1 hr and then cooled to 50° C. TEA (3.54 g, 0.035 mol) was added for neutralization and reacted for 30 mins. The mixture was cooled to 45° C. and rotary speed increased to 1030 rpm. Double distilled water was rapidly added to the mixture. After the water was dispersed, pre-diluted (by pure water) cross-linker Jeffamine T-403 (1.4 g, 0.003 mol, Huntsman, US) was added and reacted for 5 mins. Pre-diluted (by water) chain extender EDA (2.9 g, 0.048 mol) was added and reacted for 30 mins to obtain a cross-linked waterborne polyurethane emulsion with solid contents of about 30 wt %.

Experiment 10 Cell Adhesion Test for Cross-Linked Waterborne Polyurethane Film

The cross-linked waterborne polyurethane emulsion (P-40J9) synthesized in Experiment 9 was drop casted on a circular glass sheet. The glass sheet was put in an oven of 60° C. for film forming, and then the sample was put in a vacuum oven for 24 hrs to remove residual moisture.

On a clean bench, the sample was sterilized with 70% alcohol and the residual alcohol washed out twice by PBS. The sample was put in an aseptic 6-well cell culture. 150,000 fibroblasts were injected into each well cell culture and distributed uniformly. The 6-well cell culture was then placed in the cell culture incubator for 48 hours. The 6-well cell culture was taken out of the incubator and the old culture liquid removed. The surface was rinsed twice with PBS to remove the floating cells. After adding trypsin-EDTA to wet cells, the cells that adhered to the surface were separated from the cross-linked waterborne polyurethane. The number of cells were determined by a cell counter. The tissue culture polystyrene (TCPS), used for cell culture, was used as the control group in the blank test. The total cell number of TCPS was used as the standard. The ratio of the cell number of TCPS to that of the sample is the cell adhesion ratio. The results are shown in FIG. 1. TCPS, the material used for cell culture, does not cause immune reaction. The adhesion ratio of TCPS is 1. TCPS was used as the standard material for comparison with other materials. The cell adhesion ratio of waterborne polyurethane (P-40J9) was about 0.75, which is higher than that of the biomedical level product 2363 (Pellethane® 2363-80A) of Dow Chemical.

Experiment 11 Immune Reaction Analysis for Cross-Linked Waterborne Polyurethane

The cross-linked waterborne polyurethane emulsion (P-40J9) which was synthesized in Experiment 9 was drop casted on a circular glass sheet. The glass sheet was put in an oven at 60° C. for film forming, and then the sample was put in a vacuum oven for 24 hrs to remove residual moisture.

Figure 2:
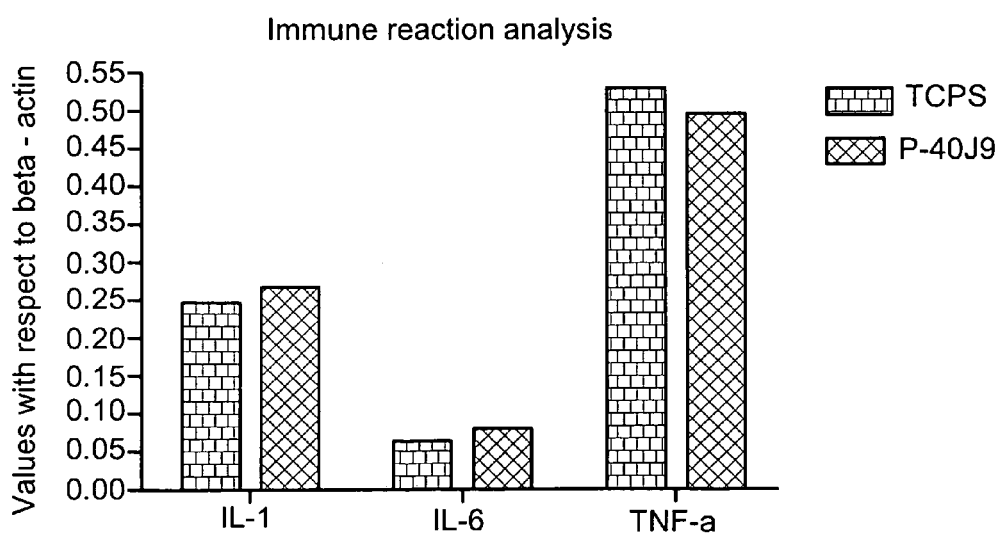
FIG. 2 shows the results of the cell immune reaction analysis for cross-linked waterborne polyurethane film in Experiment 11.

On a clean bench, the sample was sterilized with 70% alcohol and the residual alcohol washed out twice by PBS. The sample was put in an aseptic 6-well cell culture. 150,000 murine macrophages (J774 A1) were injected into each well cell culture and distributed uniformly. The E-well cell culture was then placed in the cell culture incubator for 24 hours. The 6-well cell culture was taken out of the incubator and the old culture liquid removed. The surface was rinsed twice with PBS to remove the floating cells. 1 ml of trizol was added to break the cell and the stuff was put in the microcentrifuge tube, followed by extraction of ribonucleic acid (RNA) from the cell. Complementary deoxyribonucleic acid (cDNA) was prepared by reverse transcription polymerase chain reaction (RT-PCR) and polymerase chain reaction (PCR) was carried out to enlarge the target gene. The four groups of gene, Beta-actin, interlukin-1 (IL-1), Interlukin-6 (IL-6), and Tumor necrosis factor (TNF-alpha) were isolated by electrophoresis. The resulting data was divided by the gene beta-actin showing normal distribution in cells and semi-quantitative analysis was performed. The immune test data was then obtained. The results are shown in FIG. 2. TCPS was used as the control group. The cross-linked waterborne polyurethane did not cause immune reaction from macrophages. Therefore, the expressed amount of the cross-linked waterborne polyurethane can be regarded as a base. As the expressed amount of the cross-linked waterborne polyurethane is greater than that of TCPS, it is easy to induce immune reaction. Regarding the test results of the waterborne polyurethane film, the expressed amount of the three cytokines, IL-1, IL-6, and TNF-alpha, is 0.27, 0.08, and 0.5, respectively, with respect to the gene beta-actin showing normal distribution in cells. The test results are similar to those of TCPS and lower than those of the biomedicine level product (Pellethane® 2363-80A), which means that the cross-linked waterborne polyurethane does not easily cause immune reaction.

Although the present invention has been described with reference to illustrative embodiments, it should be understood that any modifications or alterations that can easily be accomplished by persons having ordinary skill in the art will fall within the scope of the disclosure of the specification, drawings, and the appended claims.

What is claimed is:

1. A process for synthesizing a waterborne polyurethane containing biodegradable segments, comprising the steps of:
   mixing two or more long-chain polyols at 80 to 120° C., wherein at least one polyol is a biodegradable long-chain polyol;
   adding to the mixture obtained in (1) one or more aliphatic diisocyanates and reacting to form a pre-polymer A;
   adding a hydrophilic component and a water-soluble solvent with a boiling point of 50 to 80° C. and reacting at a temperature between 45° C. and the boiling point of the water-soluble solvent to form a pre-polymer B;
   optionally adding to the pre-polymer B a neutralizer;
   dispersing the mixture obtained in (4) in water to form a water-dispersed mixture; and
   adding polyamines so as to increase the molecular weight of the pre-polymer dispersed in water;
   wherein in steps (1) to (3), the ratio of the total NCO functional groups to the total OH functional groups is in a range of 1.3 to 2.6, the amount of biodegradable long-chain polyols is 15-45 wt %, based on the total solid contents, and the amount of total long-chain polyols is 60-75 wt %, based on the total solid contents, and
   wherein the biodegradable long-chain polyols comprise polylactic acid (PLA) units and/or polyglycolic acid (PGA) units.

2. The process of claim 1, wherein the polyamines include diamine chain extenders; or
   diamine chain extenders and amine cross-linkers having three functional groups;
   wherein the diamine chain extender is selected from the group consisting of ethylene diamine (EDA), butylene diamine, hexylene diamine, isophorone diamine, and mixtures thereof, and wherein the amine equivalents in the amine cross-linkers having three functional groups are 3 to 20% of the total amine equivalents.

3. The process of claim 1, wherein the long-chain polyols have a number-average molecular weight of 1,000 to 4,000 g/mol, the average number of functional groups of the long-chain polyols is about 2, and the long-chain polyol is selected from the group consisting of esters, ethers, carbonates, olefins and mixtures thereof.

4. The process of claim 1, wherein the hydrophilic component is in an amount of 2.5 to 5.0 wt %, based on the total solid contents.

5. The process of claim 1, wherein the aliphatic diisocyanate is selected from the group consisting of 4,4'-methylenebis (cyclohexyl isocyanate) ($H_{12}MDI$), isophorone diisocyanate (IPDI), 1,6-hexane diisocyanate (MI), 1,6-hexane diisocyanate dimer (MDI dimer), xylylene diisocyanate (XDI) and mixtures thereof.

6. The process of claim 2, wherein the amine cross-linkers having three functional groups are added to the water-dispersed mixture, followed by the addition of the diamine chain extenders.

7. The process of claim 1, wherein the equivalents of the hydrophilic components and the neutralizers are in a range of 0.9 to 1.1.

8. The process of claim 1, wherein the ratio of the amino equivalent of the polyamines to an equivalent of the isocyanate functional group in the pre-polymer B is 70 to 100 mole %.

9. A waterborne polyurethane containing biodegradable segments prepared by the process of claim 1.

* * * * *